United States Patent

Sueyasu

(10) Patent No.: US 11,517,180 B2
(45) Date of Patent: Dec. 6, 2022

(54) ENDOSCOPE

(71) Applicant: OLYMPUS CORPORATION, Tokyo (JP)

(72) Inventor: Hidetada Sueyasu, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 400 days.

(21) Appl. No.: 16/669,568

(22) Filed: Oct. 31, 2019

(65) Prior Publication Data

US 2020/0069153 A1 Mar. 5, 2020

Related U.S. Application Data

(63) Continuation of application No. PCT/JP2018/014601, filed on Apr. 5, 2018.

(30) Foreign Application Priority Data

May 18, 2017 (JP) .............................. JP2017-098826

(51) Int. Cl.
*A61B 1/00* (2006.01)
(52) U.S. Cl.
CPC ...... *A61B 1/00098* (2013.01); *A61B 1/00002* (2013.01); *A61B 1/00137* (2013.01)
(58) Field of Classification Search
CPC ... A61B 1/00; A61B 1/00002; A61B 1/00098; A61B 1/00137; A61B 1/0669; A61B 1/0676; A61B 1/005; A61B 1/018; A61B 1/0051; A61B 1/0052; A61B 1/0057; A61B 1/045; A61B 2017/3405; A61B 2017/3407; A61B 3/0075
See application file for complete search history.

(56) References Cited

U.S. PATENT DOCUMENTS

2007/0099500 A1* 5/2007 Pilvisto .............. A61B 1/00098
439/584

FOREIGN PATENT DOCUMENTS

| DE | 102017105178 A1 | * 9/2018 |
| EP | 1759626 B1 | 5/2013 |
| JP | S57-128128 A | 8/1982 |

OTHER PUBLICATIONS

International Search Report dated May 29, 2018 issued in PCT/JP2018/014601.

* cited by examiner

*Primary Examiner* — Michael J Carey
*Assistant Examiner* — Megan Elizabeth Monahan
(74) *Attorney, Agent, or Firm* — Scully, Scott, Murphy & Presser, P.C.

(57) ABSTRACT

An endoscope includes an insertion portion, a raising base, an operation portion, a long member configured to cause the raising base to operate, a moving mechanism configured to allow the long member to be inserted through an inside, and move in an axial direction along the long member, a fixing tool that is attachable and detachable to and from the moving mechanism, and is configured to fix the moving mechanism and the long member by being attached to the moving mechanism, and an urging member that is disposed to contact the moving mechanism and the fixing tool, is set in a direction to separate the moving mechanism and the fixing tool from each other, is configured to push the moving mechanism by bringing the fixing tool close to the moving mechanism, and has an urging force with a strength that moves the moving mechanism to a predetermined position.

9 Claims, 13 Drawing Sheets

ENDOSCOPE

CROSS REFERENCE TO RELATED APPLICATION

This application is a continuation application of PCT/JP2018/014601 filed on Apr. 5, 2018 and claims benefit of Japanese Application No. 2017-098826 filed in Japan on May 18, 2017, the entire contents of which are incorporated herein by this reference.

BACKGROUND OF THE INVENTION

1. Field of the Invention

The present invention relates to an endoscope.

2. Description of the Related Art

There has conventionally been an endoscope that raises a treatment instrument that is inserted through a distal end portion of an insertion portion from a treatment instrument insertion opening by a raising base provided at the distal end portion of the insertion portion and guides the treatment instrument to a subject. The raising base is connected to an operation lever by a wire that is inserted through the insertion portion, and swings by advance and retreat of the wire corresponding to an operation of the operation lever. The raising base and the wire are detached from the endoscope and are cleaned after the raising base and the wire are used for the subject. After the raising base and the wire are cleaned, the raising base and the wire are attached to the endoscope again.

For example, the specification of European Patent No. EP1759626B1 discloses an endoscope to which a raising base and a wire can be attached by aligning an operation lever with a predetermined position by fingers of a user so that a space between the operation portion and the raising base corresponds to a wire length, lowering the raising base, and connecting the operation portion and a proximal end portion of the wire by a connection portion.

SUMMARY OF THE INVENTION

An endoscope of one aspect of the present invention includes an insertion portion configured to be inserted into a lumen in an axial direction, a raising base that is provided at a distal end side of the insertion portion, and is configured to perform an operation of raising a distal end portion of a treatment instrument that is inserted through the insertion portion, an operation portion that is connectively provided at a proximal end side of the insertion portion, a long member that is configured to be inserted through the insertion portion and the operation portion, connect to the raising base, and move in the axial direction to operate the raising base, a moving mechanism configured to allow the long member to be inserted through an inside, and move in the axial direction along the long member, a fixing tool that is attachable and detachable to and from the moving mechanism, and is configured to fix the moving mechanism and the long member by being attached to the moving mechanism, and an urging member that is disposed to contact the moving mechanism and the fixing tool, is set in a direction to separate the moving mechanism and the fixing tool from each other, is configured to push the moving mechanism by bringing the fixing tool close to the moving mechanism, and has an urging force with a strength that moves the moving mechanism to a predetermined position.

DETAILED DESCRIPTION OF THE PREFERRED EMBODIMENT(S)

Hereinafter, an embodiment of the present invention will be described with reference to the drawings.
(Configuration of Endoscope 1)

Figure 1:
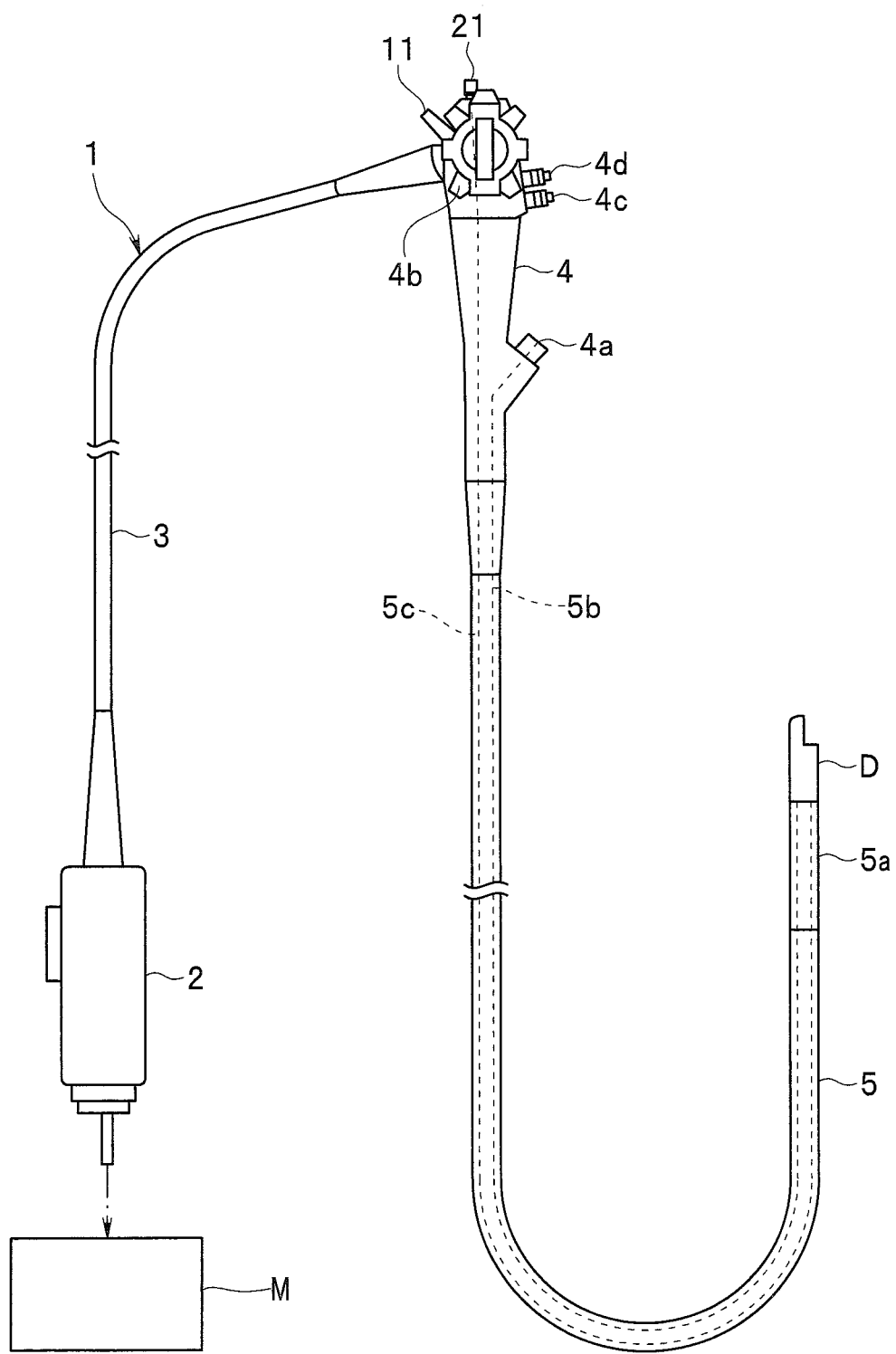
FIG. 1 is an explanatory view explaining a schematic configuration of an endoscope, according to an embodiment of the present invention.

FIG. 1 is an explanatory view explaining a schematic configuration of an endoscope 1, according to the embodiment of the present invention.

The endoscope 1 has a scope connector 2, a universal cord 3 extended from the scope connector 2, an operation portion 4 attached to the universal cord 3, an insertion portion 5 connectively provided at a distal end side of the operation portion 4, and an insertion portion distal end portion D. In other words, the operation portion 4 is connectively provided at a proximal end side of the insertion portion 5.

The scope connector 2 is configured to be able to connect to an endoscope apparatus main body M such as a power supply and a control apparatus.

The universal cord 3 has various conduits, signal lines and optical fibers not illustrated inserted through the universal cord 3, and connects the scope connector 2 and the operation portion 4.

The operation portion 4 is configured to be able to perform various operations of the endoscope 1. The operation portion 4 has a treatment instrument insertion opening 4a, an angle knob 4b, an air/water feeding button 4c and a suction button 4d.

A treatment instrument T (FIG. 2) that is protruded from the insertion portion distal end portion D via the insertion portion 5 can be inserted into the treatment instrument insertion opening 4a. The treatment instrument T is forceps, for example.

The angle knob 4b is connected to a bending portion 5a of the insertion portion 5 by a bending wire not illustrated, and is capable of inputting a bending instruction of the bending portion 5a by an operation of the user.

The air/water feeding button 4c is capable of inputting an air feeding instruction or a liquid feeding instruction to a nozzle 6c in the insertion portion distal end portion D from the endoscope apparatus main body M by an operation of the user.

The suction button 4d is capable of inputting a suction instruction of a suction target from an opening portion 7 in the insertion portion distal end portion D to the endoscope apparatus main body M by an operation of the user.

The insertion portion 5 is formed into an elongated shape and is configured to be capable of being inserted in an axial direction into a lumen of a subject. The insertion portion 5 has the bending portion 5a, a treatment instrument insertion conduit 5b and a wire insertion conduit 5c.

The bending portion 5a is provided in a vicinity of the insertion portion distal end portion D, and bends by an operation of the angle knob 4b.

The treatment instrument insertion conduit 5b is provided inside of the insertion portion 5 so that the treatment instrument T can be inserted through the treatment instrument insertion conduit 5b, and causes the treatment instrument insertion opening 4a and the insertion portion distal end portion D to communicate with each other.

The wire insertion conduit 5c is provided inside of the operation portion 4 and the insertion portion 5 so that a wire W that is a long member can be inserted through the wire insertion conduit 5c, and causes the operation portion 4 and the insertion portion distal end portion D to communicate with each other.

In the insertion portion 5, various conduits, signal lines and optical fibers are provided in addition to the treatment instrument insertion conduit 5b and the wire insertion conduit 5c, but explanation is omitted here.

Figure 2:
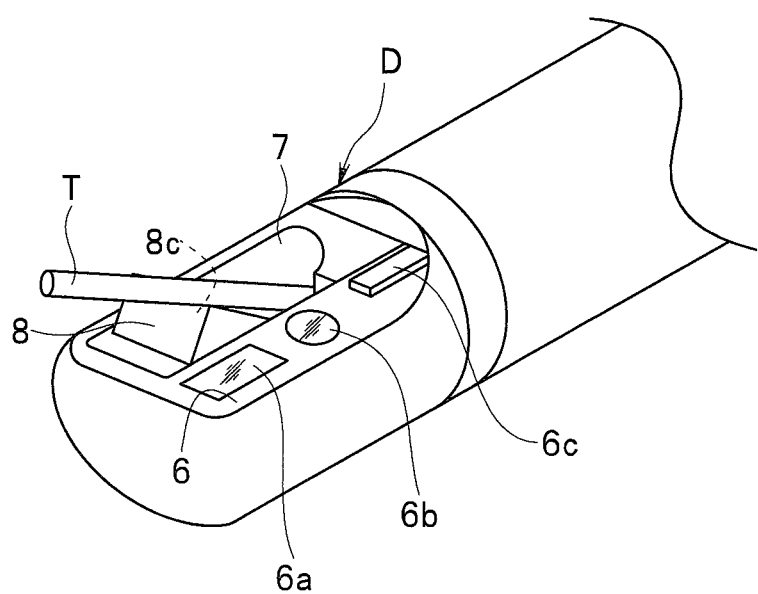
FIG. 2 is an explanatory view explaining a configuration of a distal end portion of an insertion portion of the endoscope, according to the embodiment of the present invention.

FIG. 2 is an explanatory view explaining a configuration of the insertion portion distal end portion D of the endoscope 1, according to the embodiment of the present invention.

As illustrated in FIG. 2, the insertion portion distal end portion D is formed into a cylindrical shape by a rigid member. The insertion portion distal end portion D is attached to the insertion portion 5 attachably and detachably.

The insertion portion distal end portion D has a flat portion 6, an opening portion 7, and a raising base 8.

The flat portion 6 is formed into a flat shape by cutting out a part of an outer peripheral side portion of the insertion portion distal end portion D. In the flat portion 6, an illuminating window 6a, an observation window 6b, and the nozzle 6c are provided.

The illuminating window 6a is configured by an optical lens, and irradiates a subject with illumination light that is guided from a light source of the endoscope apparatus main body M.

The observation window 6b takes in return light of the subject, and projects the return light to an image pickup device not illustrated. The image pickup device converts the return light into an image pickup signal, and outputs the image pickup signal to the endoscope apparatus main body M.

The nozzle 6c discharges gas or a liquid that is fed by the endoscope apparatus main body M.

The opening portion 7 is fouled to open to the outer peripheral side portion of the insertion portion distal end portion D. The opening portion 7 communicates with the treatment instrument insertion conduit 5b and the wire insertion conduit 5c.

The raising base 8 is provided at a distal end side of the insertion portion 5, and performs an operation of raising a distal end portion of the treatment instrument T which is inserted through the insertion portion 5. More specifically, the raising base 8 is provided in the opening portion 7, swings (rises) in accordance with to advance and retreat of the wire W, and guides the treatment instrument T so that the treatment instrument T protrudes in an outer periphery direction of the insertion portion distal end portion D. The raising base 8 has a rotation shaft hole 8a, a wire connection portion 8b, and a guide surface 8c.

The rotation shaft hole 8a is provided in a proximal end portion of the raising base 8, and is externally fitted to a rotation shaft not illustrated in the opening portion 7 to be rotatable.

The wire connection portion 8b is provided at a distal end portion of the raising base 8, and is connected to a distal end portion of the wire W that is drawn into the opening portion 7 through the wire insertion conduit 5c.

The guide surface 8c is formed into a recessed shape, and guides the treatment instrument T so that the treatment instrument T protrudes in the outer periphery direction of the insertion portion distal end portion D.

In other words, the raising base 8 is a guide member that guides the treatment instrument T so that the treatment instrument T protrudes in the outer periphery direction of the insertion portion distal end portion D. In other words, the raising base 8 changes an advancing direction of the treatment instrument T that enters into the opening portion 7 through the treatment instrument insertion conduit 5b so that the treatment instrument T protrudes in the outer periphery direction of the insertion portion distal end portion D.

(Configuration of Treatment Instrument Direction Changing Mechanism P)

Figure 3:
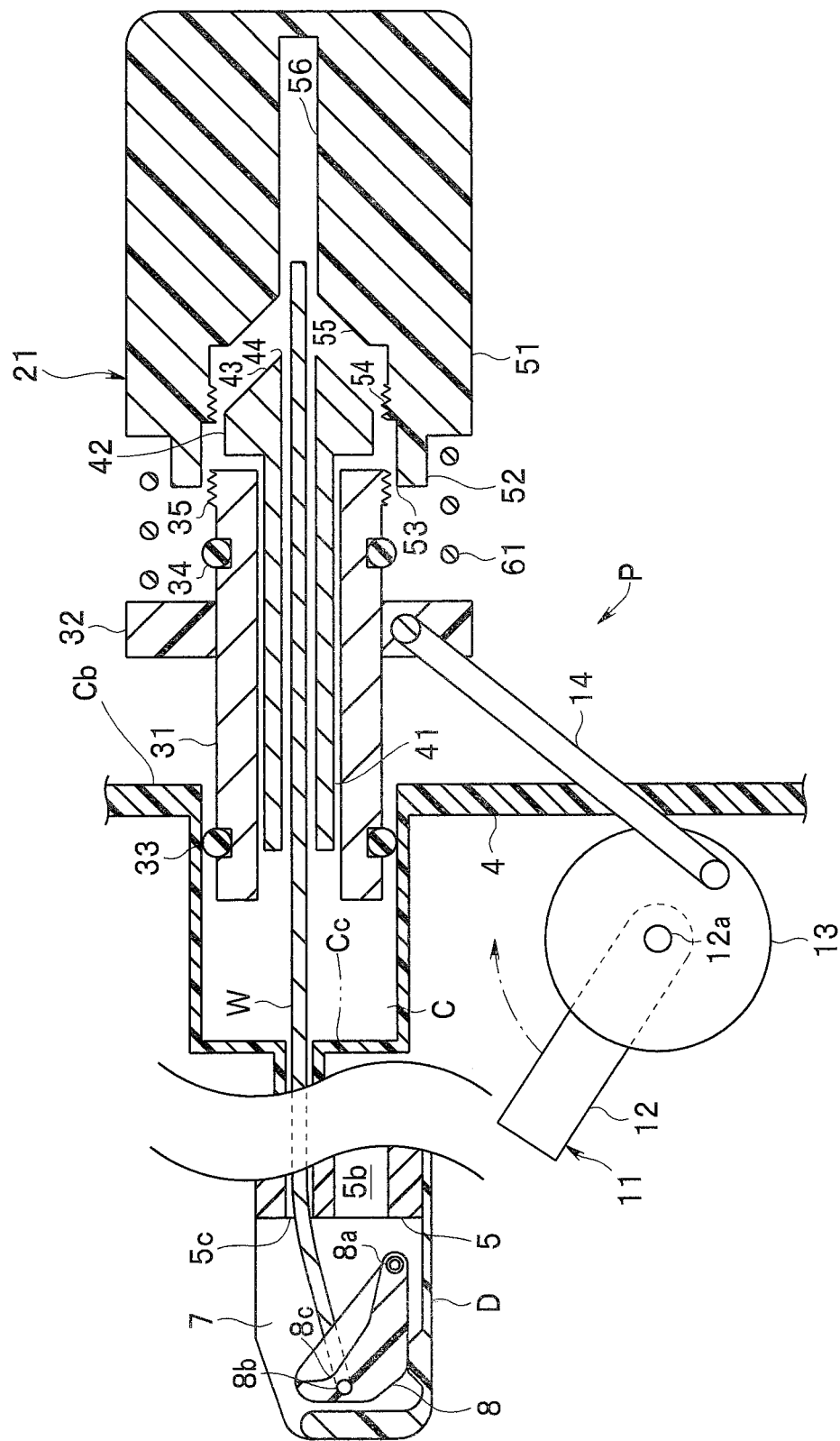
FIG. 3 is an explanatory view explaining a configuration of a treatment instrument direction changing mechanism of an endoscope, according to the embodiment of the present invention.

FIG. 3 is an explanatory view explaining a configuration of a treatment instrument direction changing mechanism P, according to the embodiment of the present invention.

The treatment instrument direction changing mechanism P is configured to be able to change a direction of the treatment instrument T in accordance with the operation of the operation portion 4. The treatment instrument direction changing mechanism P has a cylinder C, an operation lever 11, a connection portion 21, and the wire W.

The cylinder C is provided at a proximal end portion of the wire insertion conduit 5c in the operation portion 4. In the cylinder C, a proximal end is opened to outside, and a piston 31 is insertable in the cylinder C to be able to advance and retract.

The operation lever 11 is provided in the operation portion 4. To the operation lever 11, an instruction to raise or lower the raising base 8 can be inputted by the user. The operation lever 11 has a lever main body 12, a disk 13, and a rod 14.

The lever main body 12 is attached to the operation portion 4 rotatably around a lever shaft 12a so as to be capable of being operated by the user. Note that in the operation portion 4, a stopper not illustrated for stopping the swinging lever main body 12 may be provided.

The disk 13 is connected to the lever shaft 12a, and a rotational force is transmitted from the lever shaft 12a.

The rod 14 has one end connected to a peripheral rim of the disk 13, and has the other end connected to the connection portion 21. The rod 14 converts a rotational movement of the disk 13 into a linear movement and transmits the linear movement to the connection portion 21.

The connection portion 21 connects a proximal end portion of the wire W and the operation lever 11. The connection portion 21 has the piston 31, a holding member 41, a fixing tool 51, and a compression spring 61.

The piston 31 is formed into a cylindrical shape with a metal or the like as a material though the material is not specified. The piston 31 is inserted into the cylinder C, and advances and retreats in an axial direction. In the piston 31, the holding member 41 is inserted from a proximal end. The piston 31 has a flanged portion 32, O-shaped rings 33 and 34, and a screw portion 35.

The flanged portion 32 may be configured with a resin or the like as a material, for example, although the material is not specified. The flanged portion 32 is provided at an outer peripheral side portion in a vicinity of a proximal end portion of the piston 31, and is formed into a flange shape. To the flanged portion 32, the rod 14 for causing the connection portion 21 to advance and retreat is connected. When the piston 31 is pushed into the cylinder C, the flanged portion 32 butts against a peripheral rim of an opening of the cylinder C.

The O-shaped rings 33 and 34 may be configured with a rubber, a resin having elasticity or the like as a material, for example, although the material is not specified. The O-shaped ring 33 is provided at an outer peripheral side portion of a distal end portion of the piston 31 so that the piston 31 is inserted into the cylinder C with water tightness. In other words, the O-shaped ring 33 is a sealing member. Thereby, the piston 31 has the O-shaped ring 33 that is a sealing member configured to ensure water tightness between the piston 31 and the cylinder C which is a conduit through which the piston 31 is inserted.

The O-shaped ring 34 is provided at an outer peripheral side portion of a proximal end side from the flanged portion 32 so that the piston 31 is inserted into the fixing tool 51 with water tightness.

The screw portion 35 is provided at the outer peripheral side portion of the proximal end portion of the piston 31 so as to be screwed into the fixing tool 51.

The holding member 41 may be configured with a metal or the like as a material, for example, although the material is not specified. The holding member 41 is formed into a cylindrical shape, is inserted into the piston 31, and holds the wire W which is inserted through an inside. The holding member 41 has a locking portion 42, a taper surface 43, and a slotted groove 44. The holding member 41 is a collet, for example.

The locking portion 42 is provided at a proximal end portion of the holding member 41, and is formed into an outward-flange shape.

The taper surface 43 is provided at a proximal end side of the locking portion 42, and is formed so that an outside diameter becomes smaller toward a proximal end.

The slotted groove 44 is formed to extend in a distal end direction along an axis from the proximal end of the locking portion 42 to split the locking portion 42 in a circumferential direction.

The fixing tool 51 may be configured with a resin or the like as a material, for example, although the material is not specified. The fixing tool 51 is formed in a headed-cylinder shape, and is externally fitted to the proximal end portion of the piston 31. The fixing tool 51 has an annular protruded portion 52, a mounting port 53, a screw portion 54, a taper portion 55, and an extra length storage portion 56. The screw portion 54, the taper portion 55, and the extra length storage portion 56 are provided in an inner peripheral portion of the fixing tool 51.

The annular protruded portion 52 is provided at a distal end of a barrel portion. The annular protruded portion 52 has a smaller outside diameter than the barrel portion of the fixing tool 51, and is formed into an annular protruded shape.

The mounting port 53 is provided on an inner rim of the annular protruded portion 52 so as to be externally fitted to the piston 31.

The screw portion 54 is provided at a back side from the mounting port 53, and is configured to be able to be screwed onto the screw portion 35. In other words, the screw portion 54 is a connection portion.

The taper portion 55 is provided at a back side from the screw portion 54, and is formed so that an inside diameter becomes smaller toward a back side so as to butt against the taper surface 43.

The extra length storage portion 56 is provided at a back side from the taper portion 55, and communicates with the taper portion 55. The extra length storage portion 56 is capable of storing an extra length portion of the wire W.

The compression spring 61 is provided to surround an outer peripheral side portion of the annular protruded portion 52 so that a distal end contacts the flanged portion 32, and a proximal end contacts a peripheral rim of the barrel portion tip end of the fixing tool 51. In other words, the compression spring 61 is an urging member.

The wire W may be configured with a metal or the like as a material, for example, although the material is not specified. The wire W is inserted through the wire insertion conduit 5c, has the distal end portion connected to the raising base 8, and has the other end portion connected to the connection portion 21.

In other words, the long member is inserted through the insertion portion 5 and the operation portion 4, and is connected to the raising base 8, and moves in the axial direction to cause the raising base 8 to operate.

Further, the piston 31 and the holding member 41 configure a moving mechanism that allows a long member to be inserted through an inside and moves in an axial direction along the long member. The moving mechanism has the piston 31 that moves with the long member inside the conduit which is provided in the operation portion 4 and allows the long member to be inserted through the conduit.

Further, the fixing tool 51 is attachable and detachable to and from the moving mechanism, and fixes the moving mechanism and the long member by being attached to the moving mechanism. More specifically, the fixing tool 51 has a connection portion that approaches the moving mechanism against a predetermined urging force and connects to the moving mechanism. The connection portion has the screw portion 54 such as a screw that is screwed into the screw portion 35.

Further, the urging member is disposed to contact the moving mechanism and the fixing tool 51, and has a predetermined urging force in a direction to separate the moving mechanism and the fixing tool 51 from each other. The urging member elastically deforms when the fixing tool 51 approaches the moving mechanism, and generates the predetermined urging force by a restoration force. The predetermined urging force is set at such a strength that moves the moving mechanism to a predetermined position after the moving mechanism is pushed by the fingers of the user bringing the fixing tool 51 into close contact with the moving mechanism. The predetermined position is a position where lowering of the raising base 8 is instructed. More specifically, the predetermined position is a position where the flanged portion 32 is butted against a butting portion Cb that is provided at a peripheral rim of the opening of the cylinder C. Note that the predetermined position is a position where the flanged portion 32 is butted against the butting portion Cb, but may be a position where the piston 31 is butted against a butting portion Cc (two-dot chain line in FIG. 3) provided in a back portion of the cylinder C, or may be a position of the moving mechanism that is determined by the lever main body 12 being stopped by a stopper not illustrated.

Further, the fixing tool 51 is mounted to the piston 31 against the predetermined urging force of the urging member by being pressed against the piston 31. The operation lever 11 causes the long member held by the piston 31 in the axial direction.

(Operation of Treatment Instrument Direction Changing Mechanism P)

Subsequently, an operation of the treatment instrument direction changing mechanism P of the endoscope 1 of the embodiment will be described.

Figure 4:
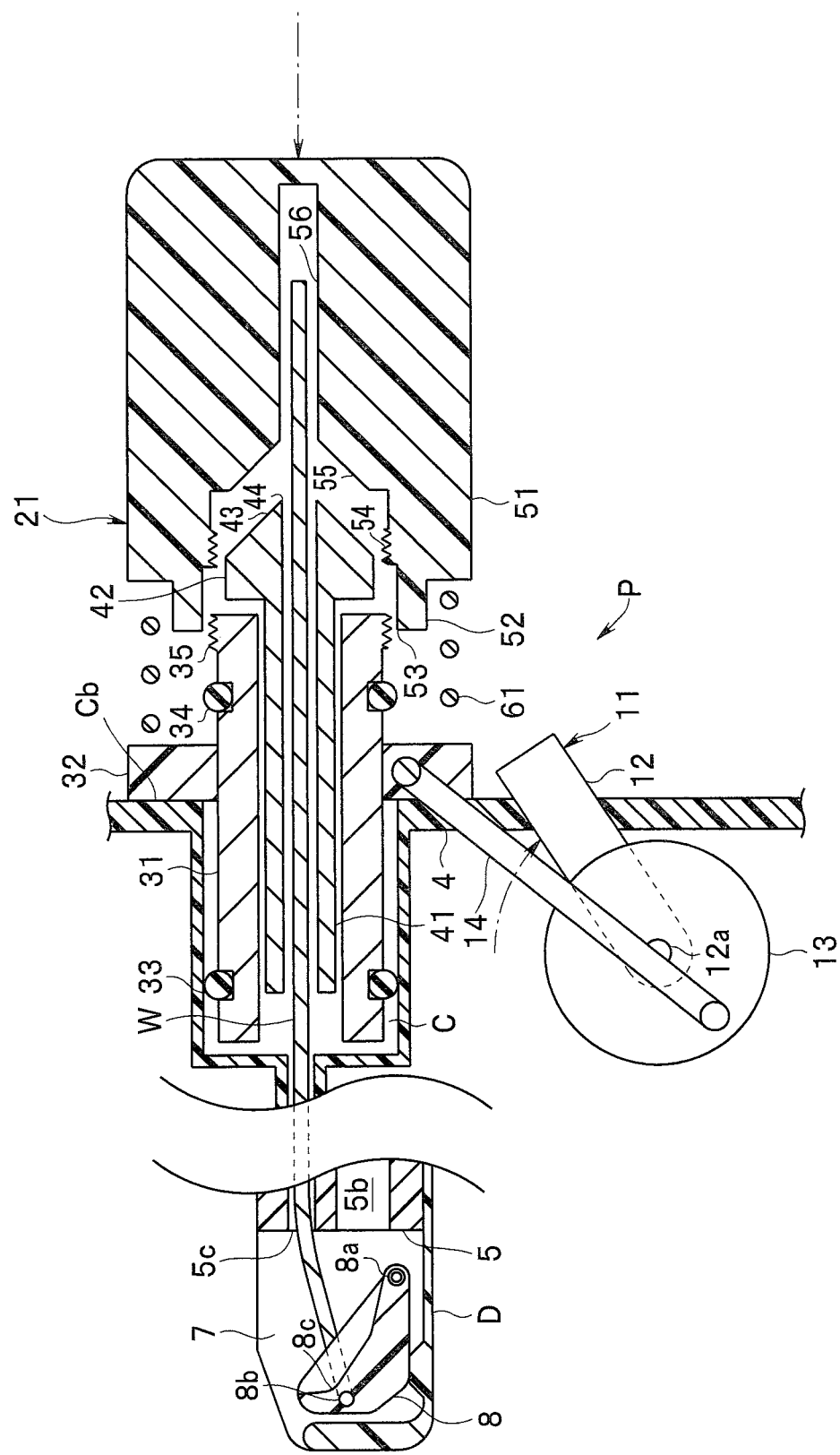
FIG. 4 is an explanatory view explaining the configuration of the treatment instrument direction changing mechanism of the endoscope, according to the embodiment of the present invention.
Figure 5:
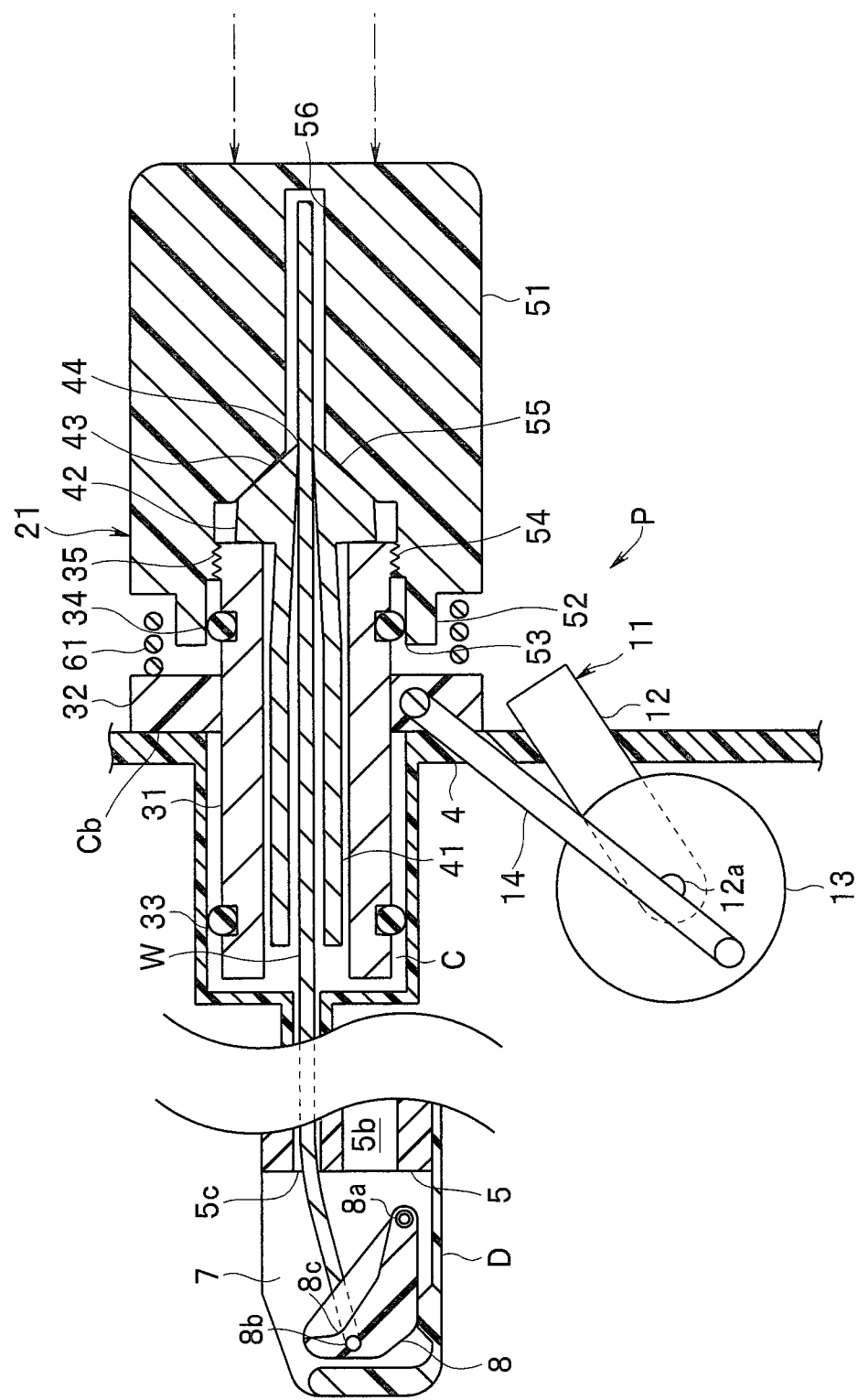
FIG. 5 is an explanatory view explaining the configuration of the treatment instrument direction changing mechanism of the endoscope, according to the embodiment of the present invention.

FIG. 4 and FIG. 5 are explanatory views explaining a configuration of the treatment instrument direction changing mechanism P of the endoscope 1, according to the embodiment of the present invention.

The user inserts the wire W which is connected to the raising base 8 into the wire insertion conduit 5c, draws out the proximal end portion of the wire W from the cylinder C, and fits the insertion portion distal end portion D to the insertion portion 5. Subsequently, the user inserts the proximal end portion of the wire W into the connection portion 21 (FIG. 3).

When the user pushes the fixing tool 51 in the distal end direction, as illustrated in FIG. 4, the compression spring 61 urges the piston 31 in the distal end direction by the predetermined urging force, with a proximal end butted against the peripheral rim of the barrel portion of the fixing tool 51, and a distal end butted against the flanged portion 32. When the piston 31 moves in the distal end direction by being urged by the compression spring 61, the disk 13 rotates by the flanged portion 32 and the rod 14, and the lever main body 12 moves to a predetermined position.

The extra length portion of the wire W that enters the fixing tool 51 is stored in the extra length storage portion 56.

When the user pushes the fixing tool 51 in the distal end direction against the predetermined urging force of the compression spring 61, as illustrated in FIG. 5, the taper portion 55 pushes the taper surface 43, and the locking portion 42 butts against the proximal end of the piston 31. When the user further pushes the fixing tool 51 in the distal end direction to cause the screw portions 35 and 54 to be screwed onto each other, the taper surface 43 is pushed in the center axis direction, the slotted groove 44 is closed, respective divided pieces of the locking portion 42 deform in such a manner as to bend in a center direction to clamp the wire W, and the holding member 41 holds the wire W.

When the screw portion 54 is unscrewed from the screw portion 35, and the fixing tool 51 is detached from the piston 31, the respective divided pieces of the holding member 41 are restored and release the wire W.

In other words, the holding member 41 holds the long member when the fixing tool 51 is attached to the moving mechanism, and releases the long member from the moving mechanism when the fixing tool 51 is detached from the moving mechanism.

Accordingly, when the user is to attach the fixing tool 51 to the piston 31 by screw, the piston 31 moves in the distal end direction, and the operation lever 11 moves to the predetermined position, and the connection portion 21 connects the operation lever 11 and the proximal end portion of the wire W so that a space between the operation portion 4 and the raising base 8 corresponds to a predetermined wire length.

According to the aforementioned embodiment, in the endoscope 1, the operation lever 11 is caused to move to the predetermined position, the space between the operation portion 4 and the raising base 8 can be caused to correspond to the predetermined wire length, and the wire W and the raising base 8 can be attached correctly, more reliably.

Modification 1 of Embodiment

In the embodiment, the compression spring 61 which is the urging member is provided to surround the outer peripheral side portion of the annular protruded portion 52, but a compression spring 191 that is an urging member may be configured to be provided inside of a fixing tool 151.

Figure 6:
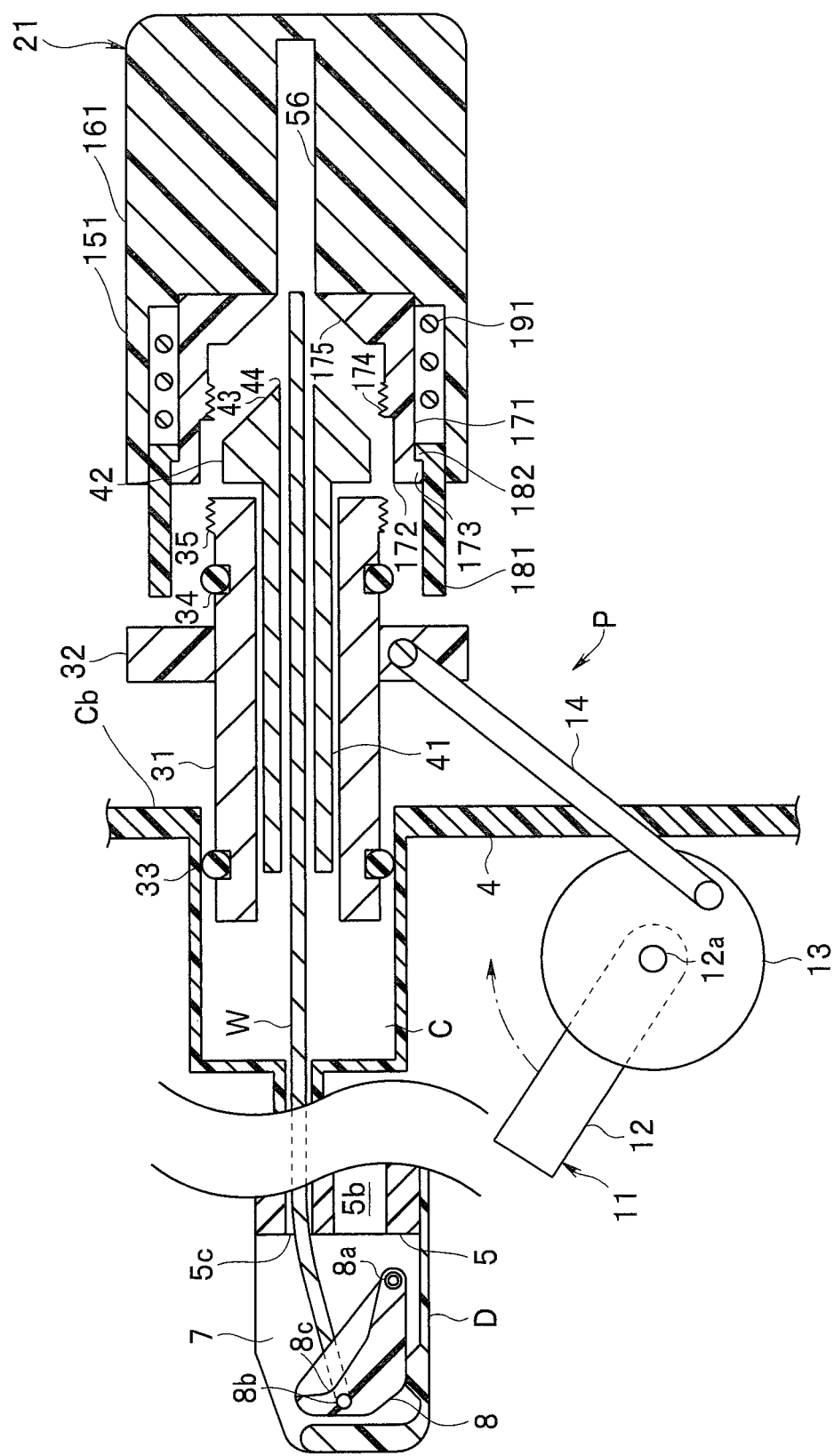
FIG. 6 is an explanatory view explaining a configuration of a treatment instrument direction changing mechanism of an endoscope, according to modification 1 of the embodiment of the present invention.
Figure 7:
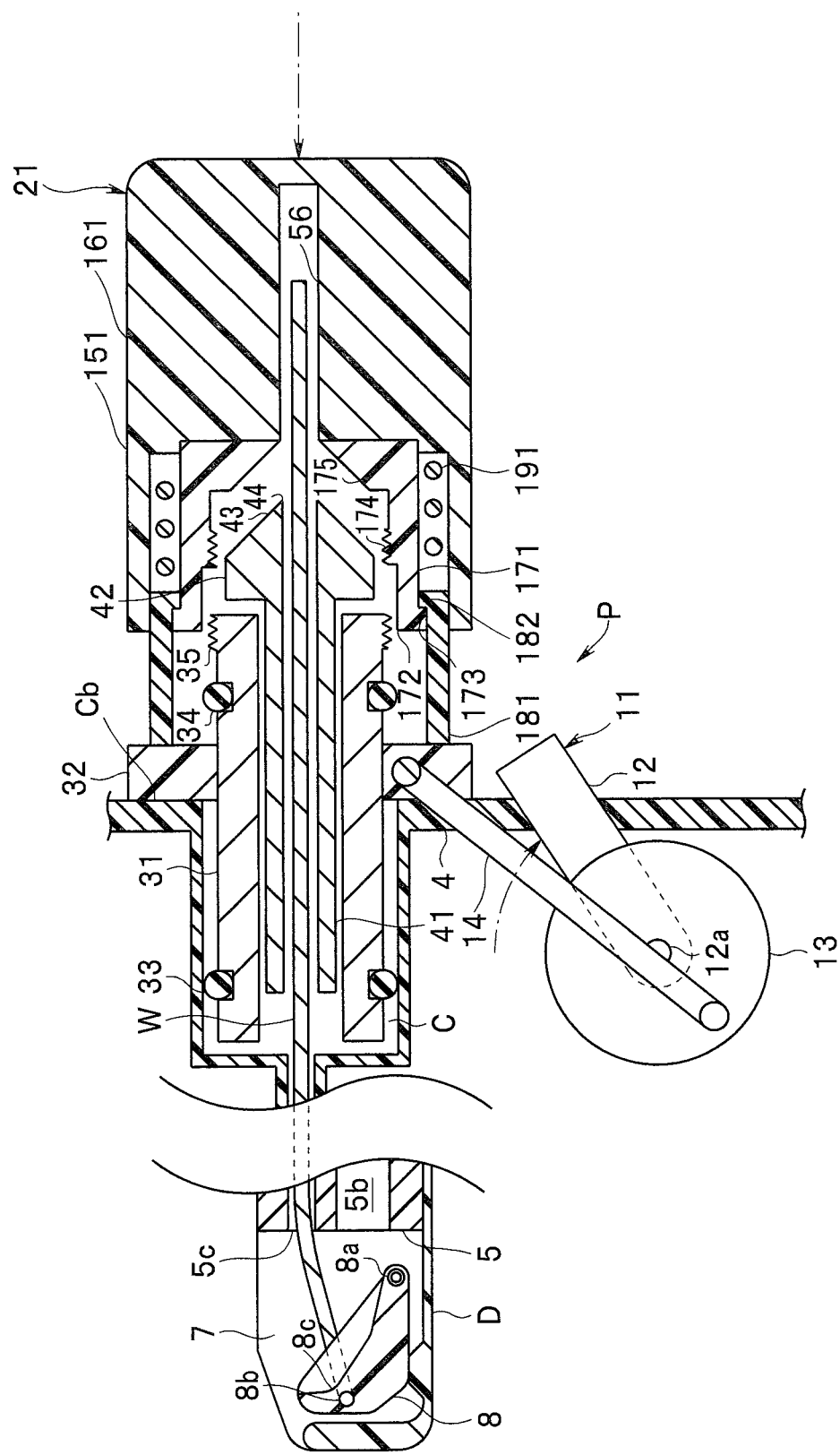
FIG. 7 is an explanatory view explaining the configuration of the treatment instrument direction changing mechanism, according to modification 1 of the embodiment of the present invention.
Figure 8:
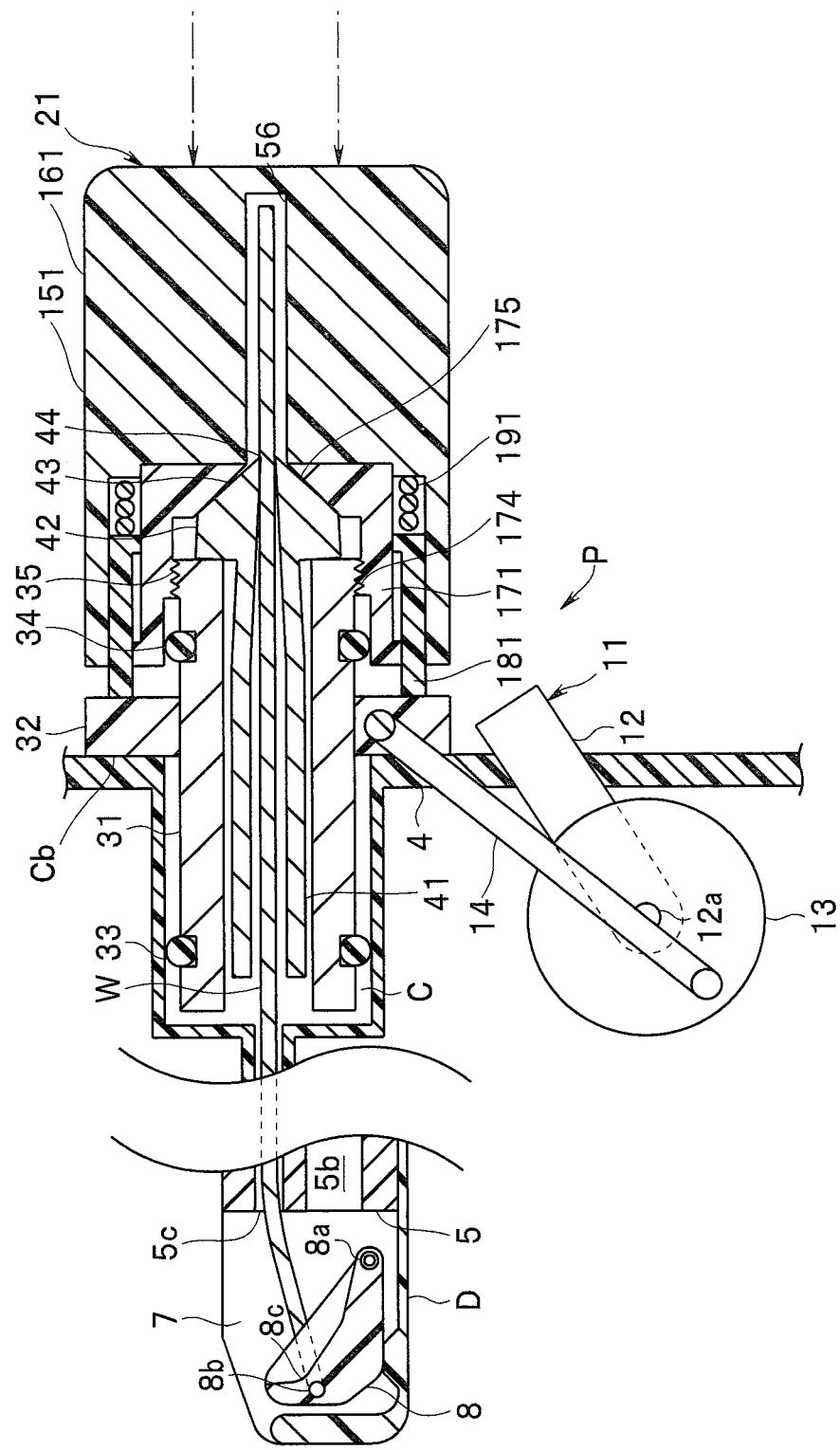
FIG. 8 is an explanatory view explaining the configuration of the treatment instrument direction changing mechanism of the endoscope, according to modification 1 of the embodiment of the present invention.

FIG. 6 to FIG. 8 are explanatory views explaining a configuration of a treatment instrument direction changing mechanism P of an endoscope 1, according to modification 1 of the embodiment of the present invention. In explanation of the present modification, explanation of the same components as components in the other embodiment and modifications will be omitted.

The connection portion 21 has a fixing tool 151.

The fixing tool 151 has a fixing tool main body 161, an inner cylinder 171, a slide cylinder 181, and the compression spring 191.

The fixing tool main body 161 is formed into a headed-cylinder shape.

The inner cylinder 171 is internally fitted to the fixing tool main body 161. The inner cylinder 171 has a mounting opening 172, a hooking portion 173, a screw portion 174, and a taper portion 175. The screw portion 174 and the taper portion 175 are provided on an inner peripheral portion of the inner cylinder 171.

The mounting opening 172 is provided at an inner rim of the inner cylinder 171 so as to be able to be externally fitted to the piston 31.

The hooking portion 173 is formed into an outward flange shape at a distal end portion of the inner cylinder 171 so as to be hooked onto the slide cylinder 181.

The screw portion 174 is provided at a back side from the mounting opening 172, and is configured to be able to be screwed onto the screw portion 35.

The taper portion 175 is provided at a back side from the screw portion 174, and is formed so that an inside diameter becomes smaller toward a back side to be butted against the taper surface 43. A proximal end of the taper portion 175 communicates with an extra length storage portion 56.

The slide cylinder 181 is provided slidably in an axial direction, in a gap between the fixing tool main body 161 and the inner cylinder 171. The slide cylinder 181 has a hooking portion 182.

The hooking portion 182 is formed into an inward flange shape, at a proximal end portion of the slide cylinder 181 so as to be able to engage with the hooking portion 173.

The compression spring 191 is provided in a gap between the fixing tool main body 161 and the inner cylinder 171, and urges the slide cylinder 181 in a distal end direction by a predetermined urging force, with a proximal end butted against an inside of the fixing tool main body 161, and a distal end butted against the proximal end of the slide cylinder 181.

When a user pushes the fixing tool 151 in a distal end direction, as illustrated in FIG. 7, the slide cylinder 181 butts against the flanged portion 32 in a distal end, and urges and moves the piston 31 in the distal end direction.

When the user pushes the fixing tool 151 in the distal end direction against the predetermined urging force of the compression spring 191, and causes the screw portions 35 and 174 to be screwed onto each other, as illustrated in FIG. 8, the slide cylinder 181 slides into the fixing tool 151, the taper portion 175 pushes the taper surface 43, and the holding member 41 holds the wire W.

Accordingly, in the endoscope 1, removal of the compression spring 191 to outside can be prevented, the operation lever 11 can be caused to move to the predetermined position, the space between the operation portion 4 and the raising base 8 can be caused to correspond to a predetermined wire length, and the wire W and the raising base 8 can be correctly attached, more reliably.

Modification 2 of Embodiment

In the embodiment and modification 1 of the embodiment, the urging members are configured by the compression springs 61 and 191, but the urging member may be configured by a hook 253.

Figure 9:
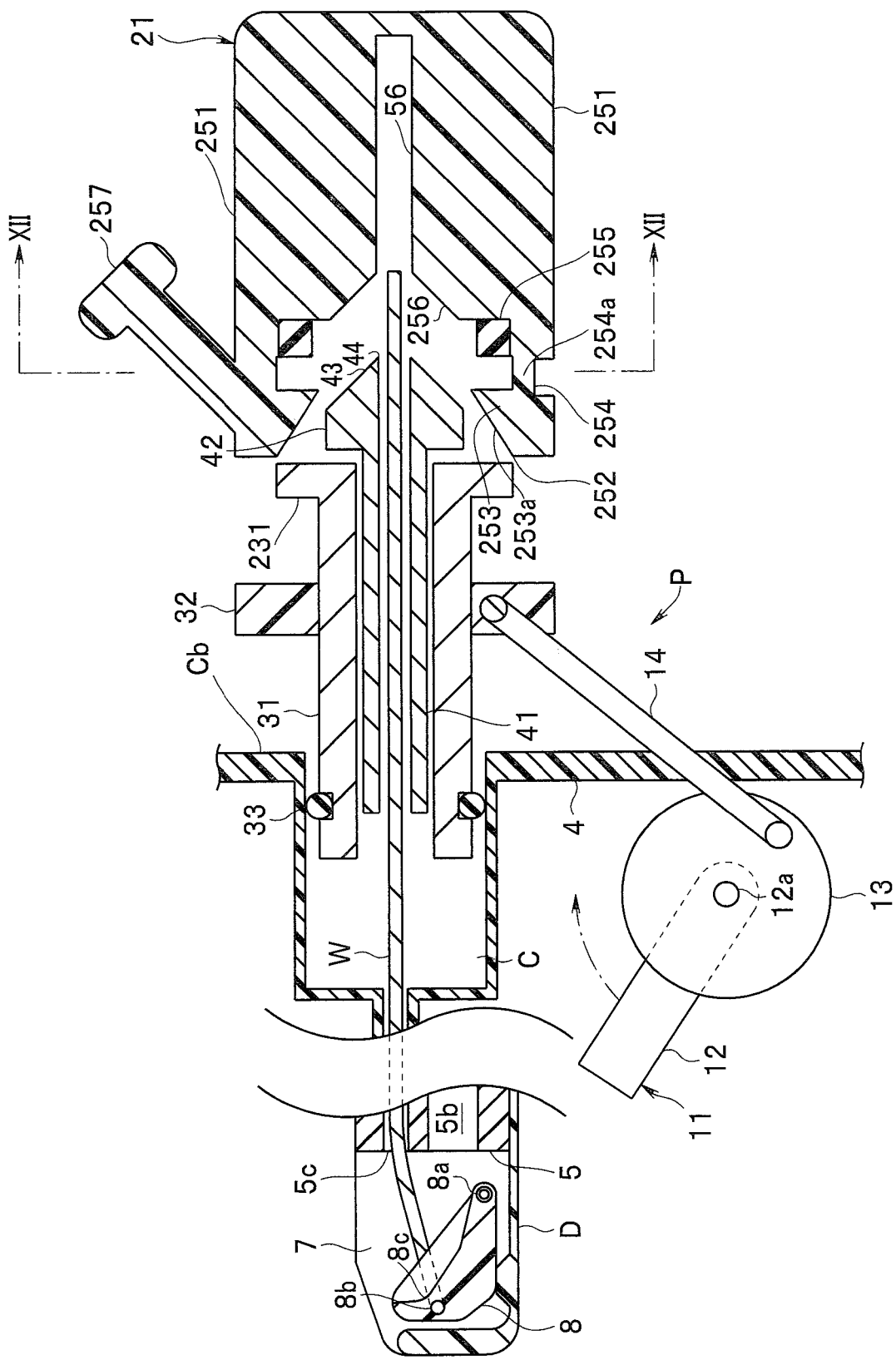
FIG. 9 is an explanatory view explaining a configuration of a treatment instrument direction changing mechanism of an endoscope, according to modification 2 of the embodiment of the present invention.
Figure 10:
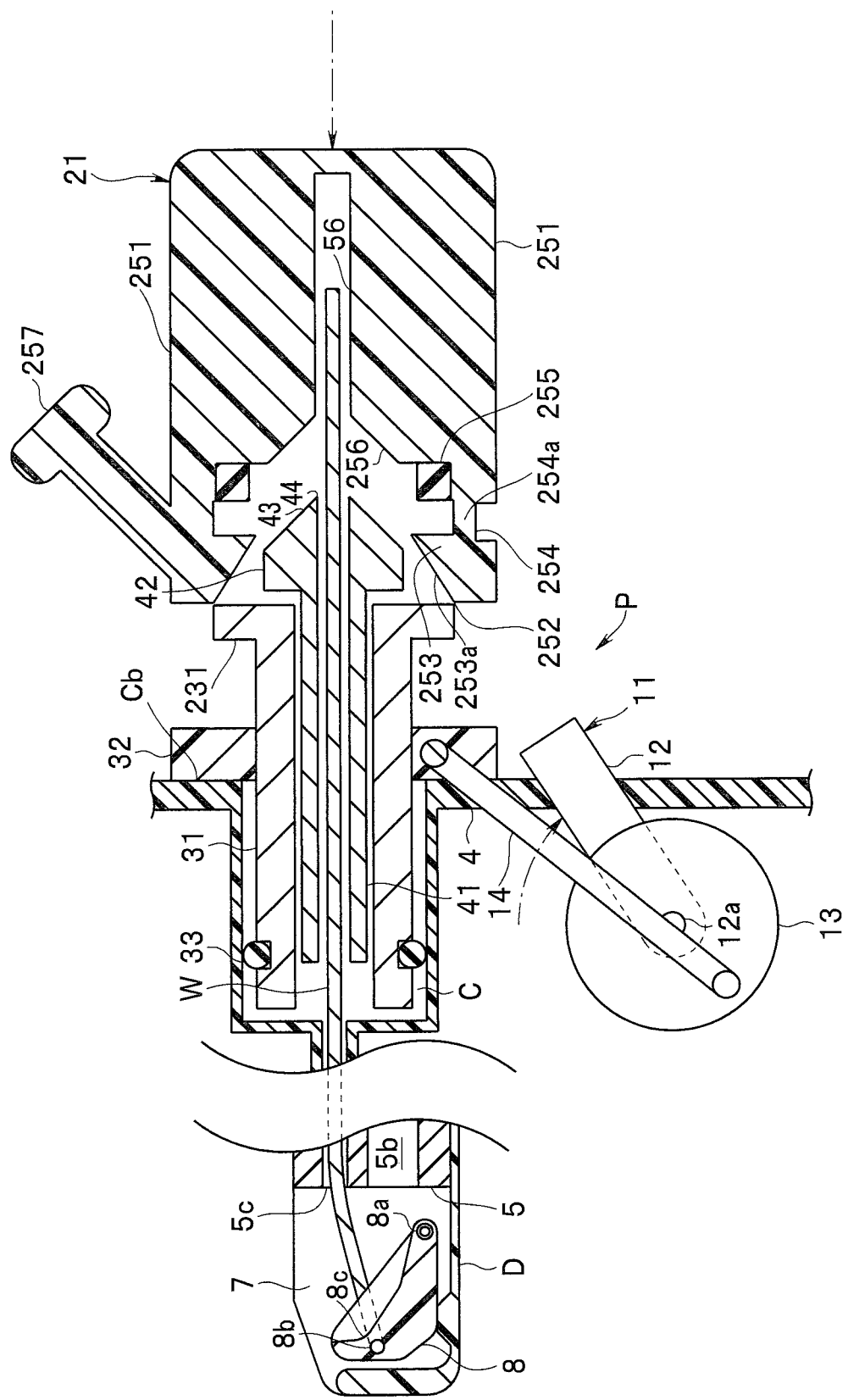
FIG. 10 is an explanatory view explaining the configuration of the treatment instrument direction changing mechanism of the endoscope, according to modification 2 of the embodiment of the present invention.
Figure 11:
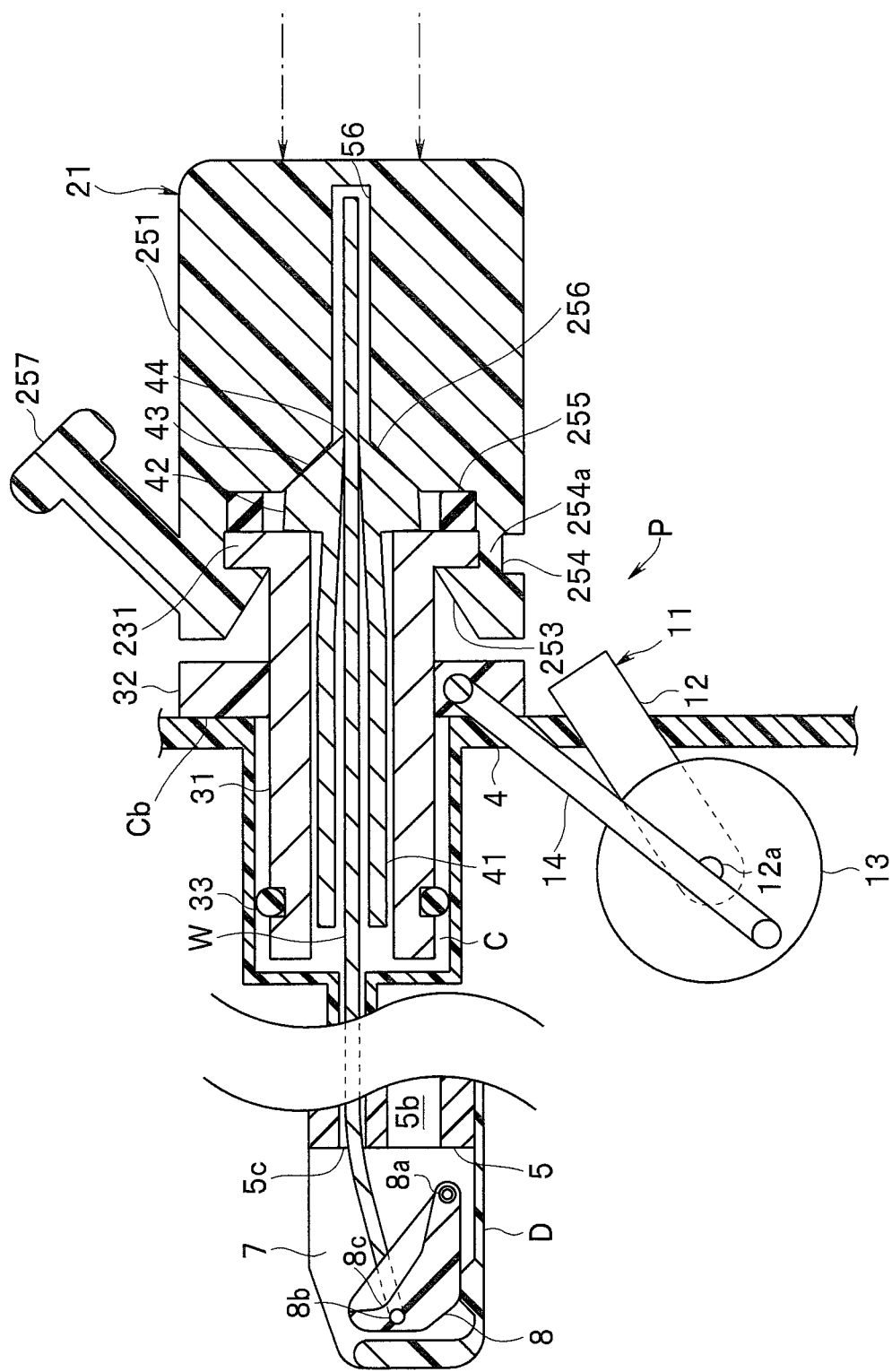
FIG. 11 is an explanatory view explaining the configuration of the treatment instrument direction changing mechanism of the endoscope, according to modification 2 of the embodiment of the present invention.
Figure 12:
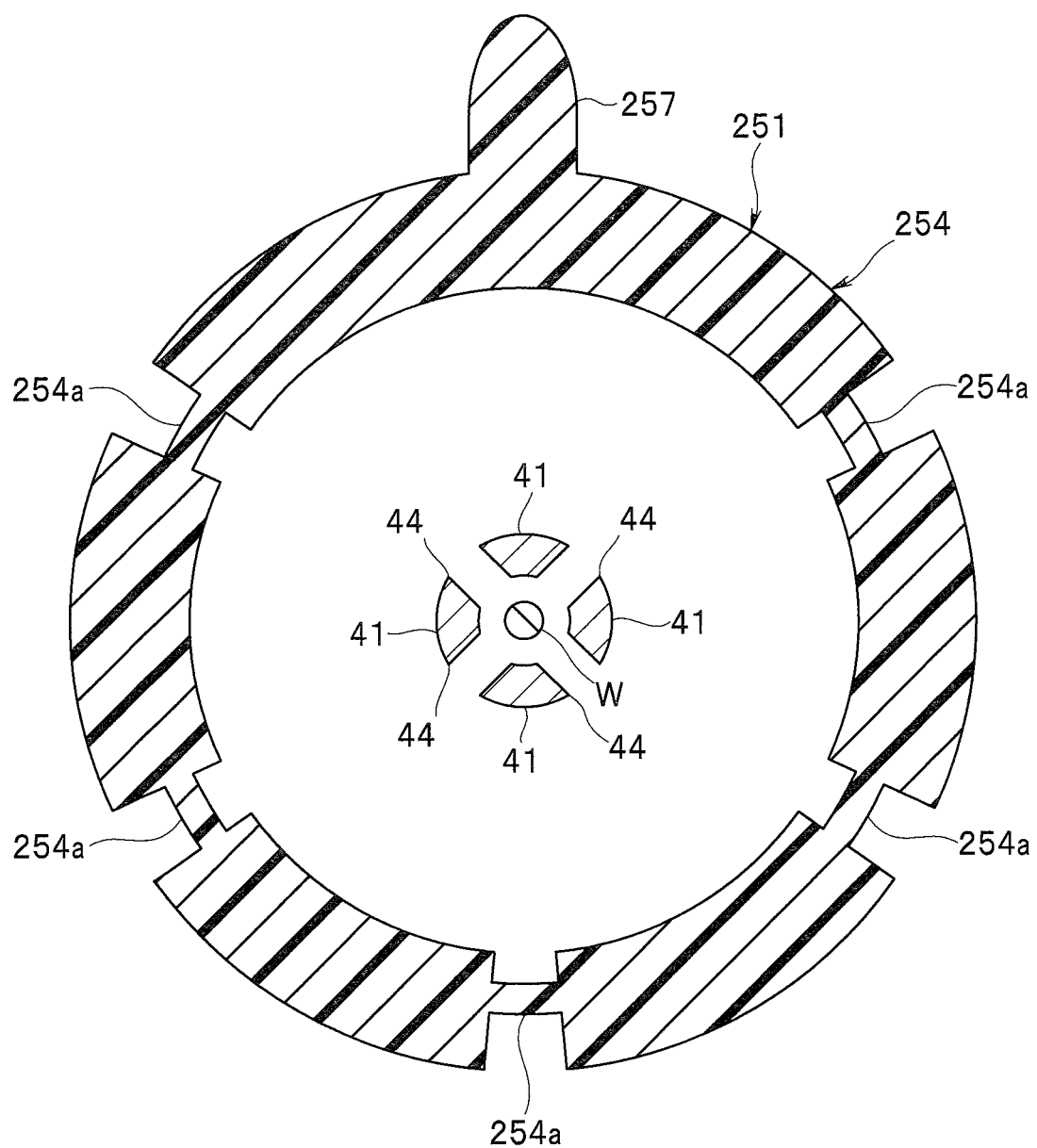
FIG. 12 is a sectional view cut along line XII-XII in FIG. 9, according to modification 2 of the embodiment of the present invention.

FIG. 9 to FIG. 11 are explanatory views explaining a configuration of a treatment instrument direction changing mechanism P of an endoscope 1, according to modification 2 of the embodiment of the present invention. FIG. 12 is a sectional view cut along line XII-XII in FIG. 9, according to modification 2 of the embodiment of the present invention. In explanation of the present modification, explanation of the same components as the components of the other embodiment and modifications will be omitted.

A piston 31 has a hook receiver 231 formed into an outward flange shape, on an outer peripheral portion of a proximal end portion.

A connection portion 21 has a fixing tool 251.

The fixing tool 251 is formed into a headed-cylinder shape. The fixing tool 251 has a mounting opening 252, the hook 253, a to-be-torn-apart section 254, a watertight member 255, a taper portion 256, and a knob 257. The watertight member 255 and the taper portion 256 are provided on the inner peripheral portion of the fixing tool 251.

The mounting opening 252 is provided on an inner rim of a distal end portion of the fixing tool 251 so as to be externally fitted to the piston 31.

The hook 253 is provided at a back side from the mounting opening 252, is configured to contact the outer peripheral portion of the piston 31, is formed to be in a protruded shape in a center direction so as to be able to be hooked on the hook receiver 231, and has a taper surface 253a formed into a taper shape so as to be butted against the hook receiver 231, at a distal end side.

The to-be-torn-apart section 254 is provided in a circumferential wall at a proximal end side from the hook 253, and has thin-walled portions 254a that are formed to be thin with spaces left in a circumferential direction so as to be easily torn apart (FIG. 12).

The watertight member 255 is provided at a back side from the to-be-torn-apart section 254 with a rubber, a resin having elasticity or the like as a material though the material is not specified. The watertight member 255 is formed into an annular shape. When the watertight member 255 butts against the hook receiver 231, the watertight member 255 brings the inside of the fixing tool 251 into a watertight state.

The taper portion 256 is provided at a back side from the to-be-torn-apart section 254, and is formed so that an inside diameter becomes smaller toward the back side so as to butt against the taper surface 43. A proximal end of the taper portion 256 communicates with the extra length storage portion 56.

The knob 257 is provided at the outer peripheral side portion of the fixing tool 251 so as to be picked by fingers of the user.

When the user pushes the fixing tool 251 in the distal end direction, and the hook receiver 231 butts against the taper surface 253a, as illustrated in FIG. 10, the hook 253 urges the hook receiver 231 in a direction to separate the hook receiver 231 from the hook 253 by a predetermined urging force generated by an elastic force, and causes the piston 31 to move in the distal end direction.

When the user pushes the hook 253 in the distal end direction against the predetermined urging force, as illustrated in FIG. 11, the hook receiver 231 is hooked on the hook 253. Further, the taper surface 43 is pressed by the taper portion 256, the slotted groove 44 is closed, and the holding member 41 holds the wire W.

When the user pulls the knob 257 by fingers, and tears the to-be-torn-apart section 254, the fixing tool 251 is detached from the piston 31.

The fixing tool 251 may be configured to be disposable. When the fixing tool 251 is configured to be disposable, the fixing tool 251 is thrown away after the to-be-torn-apart section 254 is torn.

In other words, the urging member is the hook 253 having the taper surface 253a, and the predetermined urging force is generated as the result that the moving mechanism is butted against the taper surface 253a and the hook 253 elastically deforms.

Accordingly, the operation lever 11 is caused to move to the predetermined position, the space between the operation portion 4 and the raising base 8 can be caused to correspond to the predetermined wire length, and the wire W and the raising base 8 can be correctly mounted, more reliably.

Modification 3 of Embodiment

In the embodiment and modifications 1 and 2 of the embodiment, the connection portion 21 does not push the wire W, but the connection portion 21 may be configured to push the wire W.

Figure 13:
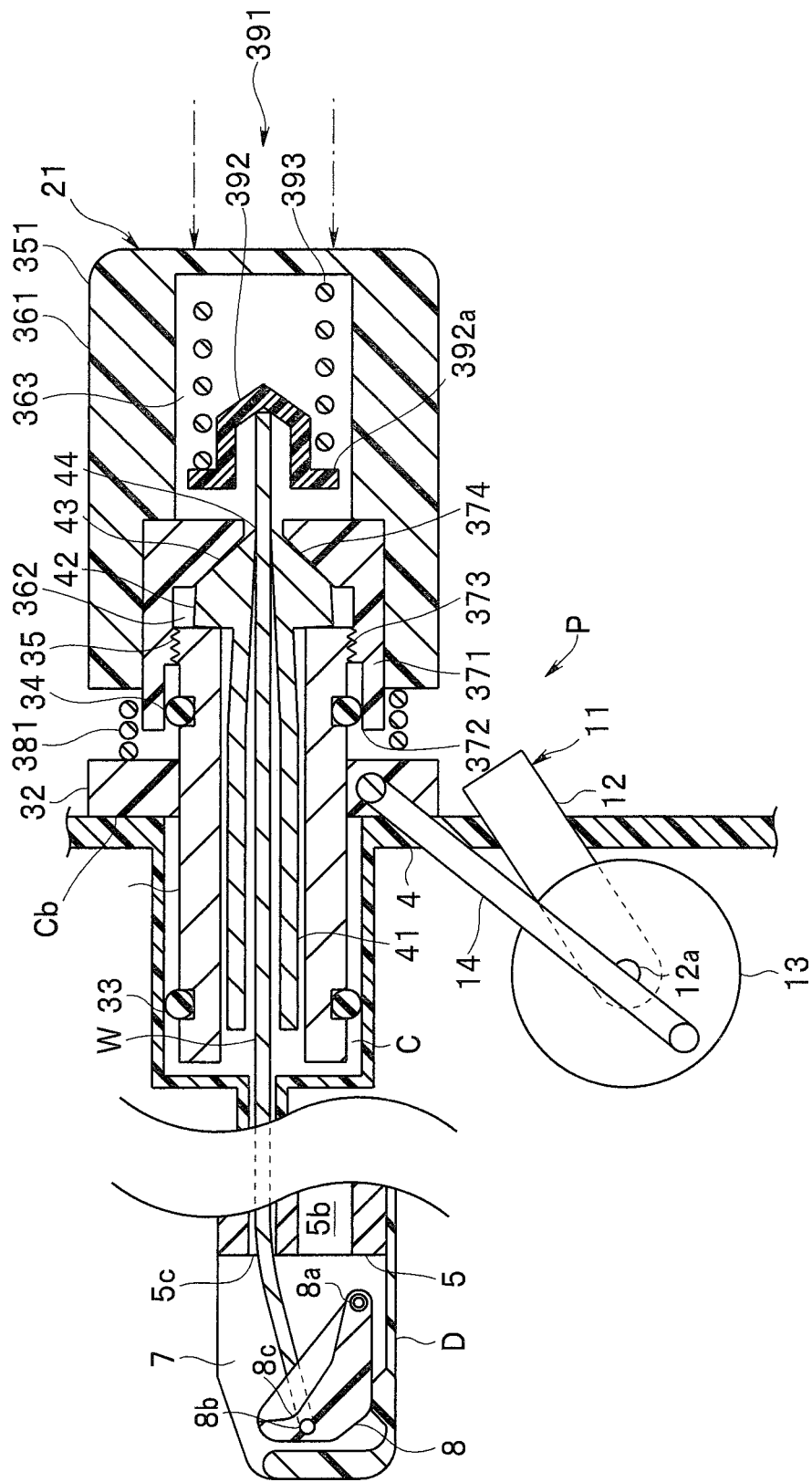
FIG. 13 is an explanatory view explaining a configuration of a treatment instrument direction changing mechanism of an endoscope, according to modification 3 of the embodiment of the present invention.

FIG. 13 is an explanatory view explaining a configuration of a treatment instrument direction changing mechanism P of an endoscope 1, according to modification 3 of the embodiment of the present invention. In explanation of the present modification, explanation of the same components as components in the other embodiment and modifications will be omitted.

The connection portion 21 has a fixing tool 351.

The fixing tool 351 has a fixing tool main body 361, an inner cylinder 371, and a wire receiver 391.

The fixing tool main body 361 is formed into a headed-cylinder shape. The fixing tool main body 361 has, inside, an inner cylinder storage chamber 362, and a wire receiver storage chamber 363 that is provided to communicate with the inner cylinder storage chamber 362 on a same axis with the inner cylinder storage chamber 362, and is formed so that an inside diameter is smaller than an inside diameter of the inner cylinder storage chamber 362.

The inner cylinder 371 is formed into a cylindrical shape, and internally fitted to the inner cylinder storage chamber 362 so that a distal end portion of the inner cylinder 371 protrudes from the fixing tool main body 361. The inner cylinder 371 has a mounting opening 372, a screw portion 373, and a taper portion 374.

The mounting opening 372 is provided at an inner rim of a distal end portion of the inner cylinder 371 so as to be externally fitted to the piston 31.

The screw portion 373 is provided at a back side from the mounting opening 372, and is configured to be able to be screwed into the screw portion 35.

The taper portion 374 is provided at a back side from the screw portion 373, and is formed so that an inside diameter becomes smaller toward the back side, so as to face the taper surface 43. A proximal end of the taper portion 374 communicates with the wire receiver storage chamber 363.

A compression spring 381 is provided to surround an outer peripheral side portion of a distal end portion of the inner cylinder 371 so that a proximal end contacts a peripheral rim of the fixing tool main body 361, and a distal end contacts the flanged portion 32.

The wire receiver 391 is configured to receive the proximal end portion of the wire W, and to be able to urge the wire W in the distal end direction. The wire receiver 391 has a cap 392 and a compression spring 393.

The cap 392 is formed into a headed-cylinder shape, and has a flanged portion 392a formed into an outward flange shape. The cap 392 is formed in such a manner that a back portion is closed so that the proximal end of the wire W butts against the back portion.

The compression spring 393 is provided to surround an outer peripheral side portion of the cap 392. The compression spring 393 urges the cap 392 in the distal end direction, with a distal end butted against the flanged portion 392a, and a proximal end butted against a back portion of the fixing tool 351.

When the user pushes the fixing tool 351 in the distal end direction, the compression spring 381 urges the flanged portion 32 in the distal end direction, and causes the piston 31 to move in the distal end direction. The proximal end portion of the wire W enters the wire receiver 391 from the proximal end of the holding member 41, and butts against the back portion of the cap 392. The compression spring 393 urges the wire W in the distal end direction via the cap 392, and the wire W that moves in the distal end direction lowers the raising base 8.

When the fixing tool 351 is further pushed in the distal end direction, and the screw portions 35 and 373 are screwed onto each other, the slotted groove 44 is closed by the taper surface 43 being pushed, and the holding member 41 holds the wire W.

Accordingly, in the endoscope 1, the raising base 8 is lowered, the operation lever 11 is caused to move to the predetermined position, a space between the operation portion 4 and the raising base 8 can be caused to correspond to a predetermined wire length, and the wire W and the raising base 8 can be correctly attached, more reliably.

Note that in the embodiment and the modifications, the raising base 8 swings in accordance with advance and retreat of the wire W, but the raising base 8 can be any raising base that operates in accordance with advance and retreat of the wire W, and is not limited to the raising base that swings. For example, the raising base 8 may be configured to perform a slide operation in the advancing and retreating direction in accordance with advance and retreat of the wire W, and raise a distal end portion of the treatment instrument T.

The present invention is not limited to the aforementioned embodiment, but various modifications, alterations and the like are enabled within the range without changing the gist of the present invention.

According to the present invention, the endoscope can be provided, in which the space between the operation portion and the raising base can be caused to correspond to the predetermined wire length, and the wire and the raising base can be correctly attached, more reliably.

What is claimed is:

1. An endoscope comprising:
    an insertion portion configured to be inserted into a lumen in an axial direction;
    a raising base provided at a distal end side of the insertion portion, the raising base being configured to perform an operation of raising a distal end portion of a treatment instrument inserted through the insertion portion;
    an operation portion connectively provided at a proximal end side of the insertion portion;
    a wire configured to:
        be inserted through the insertion portion and the operation portion;
        be connected to the raising base; and
        move in the axial direction to operate the raising base;
    a moving mechanism configured to:
        accommodate the wire through an inside; and
        move in the axial direction along the wire, the moving mechanism comprising a flanged member at an outer peripheral side portion of the moving mechanism;
    a fixing tool attachable and detachable to and from the moving mechanism, the fixing tool being configured to fix the moving mechanism and the wire by being attached to the moving mechanism; and
    a compression spring, wherein:
        the compression spring is provided to surround the outer peripheral side portion of the moving mechanism between the flanged member of the moving mechanism and the fixing tool such that the compression spring contacts the fixing tool,
        the compression spring applies a biasing force to separate the moving mechanism and the fixing tool from each other;
        the compression spring being configured to push the moving mechanism by bringing the fixing tool close to the moving mechanism,
        the biasing force having a magnitude to move the moving mechanism to a predetermined position,
        the fixing tool further comprises an inner cylinder internally fitted to an inside of the fixing tool, the compression spring is provided in a gap between the fixing tool and the inner cylinder, and one end of the compression spring contacts the inside of the fixing tool, the fixing tool further comprises a slide cylinder in the gap between the fixing tool and the inner cylinder, the slide cylinder being configured to be slidable in the axial direction, and another end of the compression spring contacts the slide cylinder to bias the slide cylinder toward the flanged member.

2. The endoscope according to claim 1, wherein the compression spring elastically deforms when the fixing tool approaches the moving mechanism.

3. The endoscope according to claim 1, wherein the fixing tool has a connection mechanism attached to the moving mechanism by moving closer to the moving mechanism against the biasing force.

4. The endoscope according to claim 3, wherein the connection mechanism is screwed onto the moving mechanism.

5. The endoscope according to claim 1, wherein the moving mechanism has a piston configured to move with the wire, inside of a conduit that is provided in the operation portion, and allows the wire to be inserted through the conduit.

6. The endoscope according to claim 5, comprising:

an operation lever configured to cause the piston to move in the axial direction, wherein the fixing tool is attached to the piston against the biasing force, and the operation lever causes the wire held by the piston to move in the axial direction.

7. The endoscope according to claim 6, wherein the piston includes a seal configured to secure water tightness between the piston and the conduit through which the piston is inserted.

8. The endoscope according to claim 1, wherein the moving mechanism includes a clamp, and the clamp holds the wire when the fixing tool is attached to the moving mechanism, and releases the wire from the moving mechanism when the fixing tool is detached from the moving mechanism.

9. The endoscope according to claim 1, wherein the inner cylinder includes a flange configured to be engaged with the slide cylinder in the gap between the fixing tool and the inner cylinder, and the slide cylinder includes another flange configured to be engaged with the flange of the inner cylinder.

* * * * *